United States Patent [19]
Nyce et al.

[11] Patent Number: 5,994,315
[45] Date of Patent: *Nov. 30, 1999

[54] LOW ADENOSINE AGENT, COMPOSITION, KIT AND METHOD FOR TREATMENT OF AIRWAY DISEASE

[75] Inventors: Jonathan W. Nyce; W. James Metzger, both of Greenville, N.C.

[73] Assignee: East Carolina University, Greenville, N.C.

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/474,497

[22] Filed: Jun. 7, 1995

[51] Int. Cl.$^6$ .......................... A61K 48/00; C12N 15/63; C12N 15/11; C12N 15/09
[52] U.S. Cl. .......................... 514/44; 435/375; 435/69.1; 435/320.1; 536/23.1; 536/24.5
[58] Field of Search .............................. 514/44; 536/23.1, 536/24.5; 935/52, 54, 8; 435/375, 69.1, 320.1

[56] References Cited

U.S. PATENT DOCUMENTS

| | | | |
|---|---|---|---|
| 5,087,617 | 2/1992 | Smith | 514/44 |
| 5,245,022 | 9/1993 | Weis et al. | 536/24.5 |
| 5,248,671 | 9/1993 | Smith | 514/44 |
| 5,264,618 | 11/1993 | Felgner et al. | 560/224 |
| 5,514,788 | 5/1996 | Bennett et al. | 536/23.1 |
| 5,521,291 | 5/1996 | Curiel et al. | 530/391.7 |

FOREIGN PATENT DOCUMENTS

| | | |
|---|---|---|
| WO 93/20200 | 10/1993 | United Kingdom . |
| 94/02605 | 2/1994 | WIPO . |
| 9530330 | 1/1995 | WIPO . |

OTHER PUBLICATIONS

J. Milligan et al.; Current Concepts in Antisense Drug Design. *J. Med. Chem.* 36(14): 1923–1937 (1993).
S. Ali et al.; Adenosine–induced bronchoconstriction in a allergic rabbit model:antagonism by theophylline aerosol. *Agents Actions* 37:165–176 (1992).
S. Ali et al.; Modification of allergen–induced airway obstruction and bronchial hyperresponsiveness in the allergic rabbit by theophylline aerosol. *Agents Actions* 37:168–170 (1992).
S. Ali et al.; Adenosine–Induced Bronchoconstriction and Contraction of Airway Smooth Muscle from Allergic Rabbits with Late–Phase Airway Obstruction: Evidence for an Inducible Adenosine $A_1$ Receptor. *J. Pharmacol. Exp. Therapeu.* 268:1328–1334 (1994).
S. Ali et al.; Adenosine receptor–mediated bronchoconstriction and bronchial hyperresponsiveness in allergic rabbit model. *Am. J. Physiol.* 266:L271–277 (1994).

Nyce, J.W., "Respirable Antisense Oligonucleotides as Novel Therapeutic Agents for Asthma and Other Pulmonary Diseases", *Exp. Opin. Invest. Drugs,* 6(9): 1–7, (1997).
Nyce, J.W. et al., "DNA Antisense Therapy for Asthma in an Animal Model", *Nature,* 385(20): 721–725, (1997).
Akhter, S. et al., "In Vivo Studies with Antisense Oligonucleotides", *Trends in Pharmacol. Sciences,* 18: 12–18, (1997).
Webb, A. et al., "BCL–2 Antisense Therapy in Patients with Non–Hodgkin Lymphoma", *Lancet,* 349(9059): 1137–41, (1997).
Yazaki, T. et al., "Treatment of Glioblastoma U–87 by Systemic Administration of an Antisense Protein Kinase C–Alpha Phosphorothioate Oligodeoxynucleotide", *Molecular Pharmacol.,* 50(2): 236–242, (1996).
Farmer, S.G. et al., "Adenosine Receptor–mediated Contraction and Relaxation of Guinea–pig Isolated Tracheal Smooth Muscle: Effects of Adenosine Antagonists", *Br. J. Pharmacol.,* 95: 371–378 (1988).
Marquardt, D.L. et al., "Aminophylline Exposure Alters Mouse Bone Marrow–derived Mast Cell Adenosine Responsiveness", *J. Allergy Clin Immunol.* 78: 462–469, (1986).
Simpson, R. U. et al, "Antisense oligonucleotide targeting against protein kinase C beta and C beta II block 1,25 –(OH)– 2D3– induced differentiation", J. Biol. Chem. 273(31):19587–19591 (1998).
Chen, CC et al, "Protein kinase Ccta mediates LPS–induced nitric oxide synthesis expression", J. Biol. Chem. 273(31): 19424–19430 (1998).
Glukhov, A. I., et al., "Inhibition of telomerase activity of melanoma cells in vitro by antisense oligodeoxynucleotides", Biochem. Biophys. Res. Commun. 248(2):.368–371 (1998).
Banasiak, K. J. and Haddard G. G., "Hypoxia–induced apoptosis: effect of hypoxia severity and role of p53 in neuronal cell death (Antisense to p53)", Brain Res. 797(2): 295–304 (1998).
Lehenkaru P et al, "Carbonic anhydrase II plays a major role in osteoclast differentiation (antisense to carbonic anhydrase II)", Exp Cell Res 242(1):128–137 (1998).
Dooley NP et al, "Apoptosis is induced in glioma cells by antisense oligonucleotide to protein kinase C alpha", Neuroreport 9(8):1727–1733 (1998).

(List continued on next page.)

*Primary Examiner*—Karen M. Hauda
*Attorney, Agent, or Firm*—Viviana Amzel; Arter & Hadden, LLP

[57] ABSTRACT

An oligonucleotide which is antisense to a mRNA encoding a polypeptide involved in airway disease(s) contains up to three adenosines per every 21 nucleotide a method of treating airway disease in a subject in need of such treatment comprises topically administering to the subject an antisense oligonucleotide in an amount effective to treat the airway disease, where the antisense oligonucleotide is essentially free of adenosine. Pharmaceutical formulations are also disclosed.

105 Claims, 1 Drawing Sheet

OTHER PUBLICATIONS

Kondo S et al, Antisense telomerase treatment: induction of distinct pathways, apoptosis and differentiation, FASEB J. 129100:801–811 (1998).

Alahari SK et al, "Novel chemically modified oligonucleotide provide potent inhibition of p–glycoprotein (an ATPase that serves as a drug efflux pump)", J. Pharmacol. Exp. Therapeut. 286(1): 419–428 (1998).

Dennis J. U., et al, "Human melanoma metastases is inhibited following ex vivo treatment with an antisense oligonucleotide to protein kinase C alpha", Cancer Lett. 128(1): 65–70 (1998).

Haeckel C., et al, "Antisense oligonucleotide inhibit urokinase", Int. J. Cancer 77(1): 153–160 (1998).

Kobayashi S. et al, "Transcription factor NF–E2 is essential for the polyploidization of Meg–J", Biochem. Biophys. Res. Commun. 247(1): 65–69 (1998).

Bennett, M.R. (1995). J. Drug Dev. Clin. Pract. 7, 225–235.

Heidenreich, O. et al (1995) Molecular Medicine Today 1, 128–133.

Gura, T. (1995) Science 270, 575–577.

De Mesmaeker, A et al (1995). Acc. Chem. Res. 28, 366–374.

Monia, B. P. et al (1992). The Journal of Biological Chemistry 267, 19954–19962.

Knight, V. et. al. (1988) Eur. Journal of Clinical Microbiology and Protections Diseases 7, 721–31 Abstract only.

Schreier, H. (1994). Pharmaceutica Acta Helvetiae 68, 145–59 Abstract only.

Mao, L. et al (1994). Circulation 90 (4 Part 2), I474. Abstract only.

LOW ADENOSINE AGENT, COMPOSITION, KIT AND METHOD FOR TREATMENT OF AIRWAY DISEASE

This invention was made at least partially with United States Government support under grant RO1CA47217-06 from the National Cancer Institute. The Government has certain rights to this invention.

FIELD OF THE INVENTION

This application concerns a method of administering antisense oligonucleotides essentially free of adenosine as a treatment for lung diseases.

BACKGROUND OF THE INVENTION

Antisense oligonucleotides have received considerable theoretical consideration as potentially useful pharmacologic agents in human disease. R. Wagner, Nature 372, 333–335 (1994). However, practical applications of these molecules in actual models of human disease have been elusive. One important consideration in the pharmacologic application of these molecules is route of administration. Most experiments utilizing antisense oligonucleotides in vivo have involved direct application to limited regions of the brain (see C. Wahlestedt, Trends in Pharmacological Sciences 15, 42–46 (1994); J. Lai et al., Neuroreport 5, 1049–1052 (1994); K. Standifer et al., Neuron 12, 805–810 (1994); A. Akabayashi et al., Brain Research 21, 55–61 (1994)), or to spinal fluid (see e.g. L. Tseng et al., European J. Pharmacol. 258, R1–3 (1994); R. Raffa et al., European J. Pharmacol. 258, R5–7 (1994); F. Gillardon et al., European J. Neurosci. 6, 880–884 (1994)). Such applications have limited clinical utility due to their invasive nature.

The systemic administration of antisense oligonucleotides also poses significant problems with respect to pharmacologic application, not the least of which is the difficulty in targeting disease-involved tissues. In contrast, the lung is an excellent potential target for antisense oligonucleotide application since it may be approached noninvasively and in a tissue-specific manner. However, the technology involved in delivering antisense agents to the lung remains relatively undeveloped, and potential problems related to the application of antisense agents to the lung remain unexplored.

Adenosine may constitute an important mediator of bronchial asthma. R. Pauwels et al., Clinical & Exp. Allergy 21 Suppl. 1, 48–55 (1991); S. Holgate et al., Annals of the New York Acad. Sci. 629, 227–236 (1991). The potential role of adenosine in human asthma is supported by the experimental finding that, in contrast to normal individuals, asthmatic individuals respond to aerosolized adenosine with marked bronchoconstriction. M. Church and S. Holgate, Trends Pharmacol. Sci. 7, 49–50 (1986); M. Cushley et al., Br. J. Clin. Pharmacol. 15, 161–165 (1983). Similarly, asthmatic rabbits produced using the dust mite allergic rabbit model of human asthma also were shown to respond to aerosolized adenosine with marked bronchoconstriction, while non asthmatic rabbits showed no response. S. Ali et al., Agents Actions 37, 165–176 (1992). Recent work using this model system has suggested that adenosine-induced bronchoconstriction and bronchial hyperresponsiveness in asthma are mediated primarily through the stimulation of adenosine receptors. S. Ali et al., J. Pharmacol. Exp. Ther. 268, 1328–1334 (1994); S. Ali et al., Am. J. Physiol 266, L271–277 (1994).

Adenosine has also been shown to cause adverse effects, including death, when administered therapeutically for other diseases and conditions in subjects with previously undiagnosed hyperreactive airways. See e.g., R. P. Cowell et al., Brit. Heart J. 71(6),569–71 (1994); D. J. Pennell et al., Europ. J. Nuclear Med. 21(2), 170-2 (1994); R. Reed et al., Am. J. Emerg. Med. 21(4), 453 (1992).

SUMMARY OF THE INVENTION

The present invention relates to a method of treating airway disease in a subject in need of such treatment. The method comprises administering an antisense oligonucleotide essentially free of adenosine to the lungs of the subject in an amount effective to treat the airway disease.

The present invention relates to a pharmaceutical composition, comprising, a pharmaceutically acceptable carrier, and an antisense oligonucleotide essentially free of adenosine.

The present invention also relates to the use of an antisense oligonucleotide essentially free of adenosine for the preparation of a medicament for treating airway disease in a subject in need of such treatment.

BRIEF DESCRIPTION OF THE DRAWINGS

FIG. 1 illustrates the effects of $A_1$ adenosine receptor antisense oligonucleotides and mismatch control antisense oligonucleotides on the dynamic compliance of the bronchial airway in a rabbit model.

FIG. 2 illustrates the specificity of $A_1$ adenosine receptor antisense oligonucleotides as indicated by the $A_1$ and $A_2$ adenosine receptor number present in $A_1$ adenosine receptor antisense oligonucleotide-treated airway tissue.

DETAILED DESCRIPTION OF THE INVENTION

Figure 1:
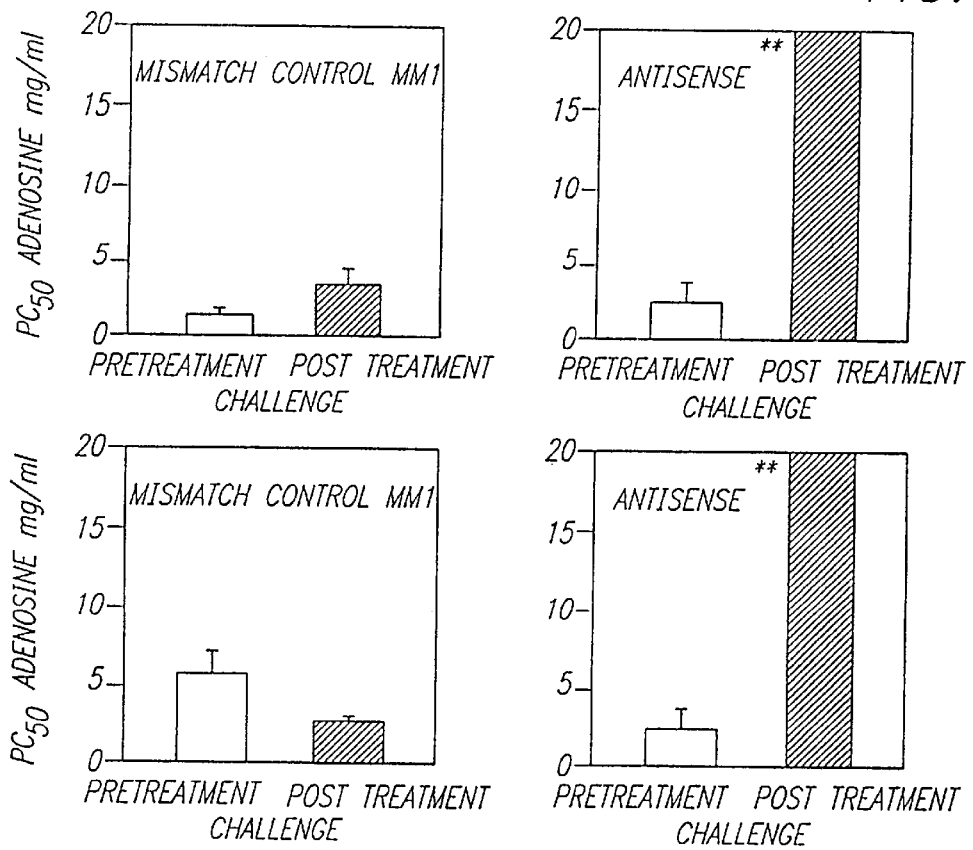
FIG. 1 and FIG. 2 demonstrate that antisense oligonucleotides can be utilized as effective agents in the treatment or prevention of airway diseases.

Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code, in accordance with 37 CFR §1.822 and established usage. See, e.g., PatentIn User Manual, 99–102 (Nov. 1990)(U.S. Patent and Trademark Office, Office of the Assistant Commissioner for Patents, Washington, D.C. 20231); U.S. Pat. No. 4,871,670 to Hudson et al. at Col. 3 lines 20–43 (applicants specifically intend the disclosures of this and all other patents and other references cited in this patent are incorporated herein by reference).

The method of the present invention may be used to treat airway disease in a subject for any reason, with the intention that adenosine content of antisense compounds be eliminated or reduced so as to prevent its liberation upon antisense degradation. Such liberation may cause serious, even life-threatening, bronchoconstriction in patients with hyperreactive airways. Examples of airway diseases that may be treated by the method of the present invention include cystic fibrosis, asthma, chronic obstructive pulmonary disease, bronchitis, and other airway diseases characterized by an inflammatory response.

Antisense oligonucleotides to the $A_1$ and $A_3$ receptors are shown to be effective in the downregulation of $A_1$ or $A_3$ in the cell. One novel feature of this treatment, as compared to traditional treatments for adenosine-induced bronchoconstriction, is its direct administration to the lungs.

Additionally, a receptor protein itself as is the case with treatments where the drug merely interacts with the receptor. The selective characteristic of the present oligonucleotide results in a reduction in toxicity. Other proteins that may be targeted with antisense agents for the treatment of lung conditions include, but are not limited to: human A2a adenosine receptor, human A2b adenosine receptor, human IgE receptor β, human Fc-epsilon receptor CD23 antigen, human histidine decarboxylase, human beta tryptase, human tryptase-I, human prostaglandin D synthase, human cyclooxygenase-2, human eosinophil cationic protein, human eosinophil derived neurotoxin, human eosinophil peroxidase, human intercellular adhesion molecule-1 (ICAM-1), human vascular cell adhesion molecule 1 (VCAM-1), human endothelial leukocyte adhesion molecule (ELAM-1), human P selectin, human endothelial monocyte activating factor, human IL-3, human IL-4, human IL-5, human IL-6, human IL-8, human monocyte-derived neutrophil chemotactic factor, human neutrophil elastase, human neutrophil oxidase factor, human cathepsin G, human defensin 1, human defensin 3, human macrophage inflammatory protein-1-alpha, human muscarinic acetylcholine receptor HM1, human muscarinic acetylcholine receptor HM3, human fibronectin, human GM-CSF, human tumor necrosis factor α, human leukotriene C4 synthase, human major basic protein, and human endothelin 1. In these latter targets, and in target genes in general, it is particularly imperative to eliminate or reduce the adenosine content of the corresponding antisense oligonucleotide to prevent their breakdown products from liberating adenosine.

As used herein, the term "treat" or "treating" a lung disease refers to a treatment which decreases the likelihood that the subject administered such treatment will manifest symptoms of the lung disease. The term "downregulate" thus refers to inducing a decrease in production, secretion or availability (and thus a decrease in concentration) of the targeted intracellular protein.

The present invention is concerned primarily with the treatment of human subjects but may also be employed for the treatment of other mammalian subjects, such as dogs and cats, for veterinary purposes. Targeted proteins are preferably mammalian and more preferably of the same species as the subject being treated.

In general, "antisense" oligonucleotide refers to the use of small, synthetic oligonucleotides, resembling single-stranded DNA, to inhibit gene expression by inhibiting the function of the target messenger RNA (mRNA). Milligan, J. F. et al., *J. Med. Chem.* 36 (14) , 1923–1937 (1993). The present invention thus, is intended for inhibition of gene expression of the $A_1$ or $A_3$ adenosine receptor desired. Gene expression is inhibited through hybridization to coding (sense) sequences in a specific messenger RNA (mRNA) target, e.g., by hydrogen bonding according to Watson-Crick base pairing rules. The mechanism of antisense inhibition is that the exogenously applied oligonucleotides decrease the mRNA or protein levels of the target gene or cause changes in the growth characteristics or shapes of the cells. Id. See also Helene, C. and Toulme, J., *Biochim. Biophys. Acta* 1049, 99–125 (1990); Cohen, J. S., Ed., *Oligodeoxynucleotides as Antisense Inhibitors of Gene Expression*; CRC Press:Boca Raton, Fla. (1987).

As used herein, "antisense oligonucleotide" is defined as a short sequence of synthetic nucleotides that (1) hybridizes to any coding sequence in an mRNA which codes for the targeted protein, according to hybridization conditions described below, and (2) upon hybridization causes a decrease in gene expression of the targeted protein.

The mRNA sequence of the $A_1$ or $A_3$ adenosine receptor is derived from the DNA base sequence of the gene expressing either the $A_1$ or $A_3$ adenosine receptor. The sequence of the genomic human $A_1$ adenosine receptor is known and is disclosed in U.S. Pat. No. 5,320,963 to G. Stiles et al. The $A_3$ adenosine receptor has been cloned, sequenced and expressed in rat (see F. Zhou et al., *Proc. Nat'l Acad. Sci. USA* 89:7432 (1992)) and human (see M. A. Jacobson et al., U.K. Patent Application No. 9304582.1 (1993)). The antisense oligonucleotides that downregulate the production of the $A_1$ or $A_3$ adenosine receptor may be produced in accordance with standard techniques.

The antisense oligonucleotide of this invention has a sequence binding specifically with any sequence of an mRNA molecule which encodes an airway disease-associated protein and prevents translation of the mRNA molecule.

Also part of this invention are chemical analogs of oligonucleotides in which, for example, the phosphodiester bonds have been modified, e.g., to the methylphosphonate, the phosphotriester, the phosphorothioate, the phosphorodithioate, or the phosphoramidate, so as to render the oligonucleotide more stable in vivo. The naturally occurring phosphodiester linkages in oligonucleotides are susceptible to degradation by endogenously occurring cellular nucleases, while many analogous linkages are highly resistant to nuclease degradation. See Milligan et al., and Cohen, J. S., supra. The use of a "3'-end cap" strategy by which nuclease-resistant linkages are substituted for phosphodiester linkages at the 3' end of the oligonucleotide protect oligonucleotide from degradation. See Tidd, D. M. and Warenius, H. M., *Br. J. Cancer* 60, 343–350 (1989); Shaw, J. P. et al., *Nucleic Acids Res.* 19, 747–750 (1991). Phosphoroamidate phosphorothioate, and methylphosphonate linkages all function adequately in this manner. More extensive modification of the phosphodiester backbone has been shown to impart stability and may allow for enhanced affinity and increased cellular permeation of oligonucleotides. See Milligan, et al., supra. Many different chemical strategies have been employed to replace the entire phosphodiester backbone with novel linkages. Id. The analogues of the oligonucleotides of the invention include phosphorothioate, phosphorodithioate, methylphosphonate, phosphoramidate, boranophosphate, phosphotriester, formacetal, 3'-thioformacetal, 5'-thioformacetal, 5'-thioether, carbonate, 5'-N-carbamate, sulfate, sulfonate, sulfamate, sulfonamide, sulfone, sulfite, sulfoxide, sulfide, hydroxylamine, methylene(methylimino) (MMI) or methyleneoxy(methylimino) (MOMI) linkages. Phosphorothioate and methylphosphonate-modified oligonucleotides are particularly preferred because of their availability for automated oligonucleotide synthesis. Id. Where appropriate, the antisense oligonucleotides may be administered in the form of pharmaceutically acceptable salts.

Antisense oligonucleotides may be of any suitable length e.g., from about 10 to 60 nucleotides in length, depending on the particular target being bound and their mode of delivery. Preferably the antisense oligonucleotide is directed to an mRNA region containing a junction between intron and exon. Where the antisense oligonucleotide is directed to an intron/exon junction, it may either entirely overlie the junction or may be sufficiently close to the junction to inhibit the splicing out of the intervening exon during processing of precursor mRNA to mature mRNA e.g., with the 3' or 5' terminus of the antisense oligonucleotide being positioned within about, for example, 10, 5, 3, or 2 nucleotides of the intron/exon junction.

When practicing the present invention, the antisense nucleotides administered may be related in origin to the species to which it is administered. When treating humans, the antisense may be derived from human sequences if desired.

Pharmaceutical compositions provided herein comprise the antisense oligonucleotide as given above. These compositions are administered in amounts effective to reduce the expression of an adenosine receptor, such as the $A_1$ or $A_3$ adenosine receptor by passing e.g., through a cell membrane and binding specifically with mRNA encoding an $A_1$ or $A_3$ adenosine receptor in the cell and prevent its translation. Such compositions are provided in a suitable pharmaceutically acceptable carrier e.g., sterile pyrogen-free saline solution. The antisense oligonucleotides may additionally be formulated with a hydrophobic carrier capable of passing through a cell membrane, e.g., in a liposome, with the liposomes carried in a pharmaceutically acceptable aqueous carrier. The oligonucleotides may also be coupled to a substance which inactivates mRNA, such as a ribozyme. The present oligonucleotides may be administered to a subject to inhibit the activation of $A_1$ or $A_3$ adenosine receptors, which subject is in need of such treatment for any of the reasons discussed herein. Furthermore, the pharmaceutical formulation may also contain chimeric molecules comprising antisense oligonucleotides attached to molecules which are known to be internalized by cells. These oligonucleotide conjugates utilize cellular uptake pathways to increase the cellular concentrations of oligonucleotides. Examples of macromolecules used in this manner include transferrin, asialoglycoprotein (bound to oligonucleotides via polylysine) and streptavidin.

In the pharmaceutical formulation the antisense compound may be contained within a lipid particle or vesicle, such as a liposome or microcrystal. The lipid particles may be of any suitable structure, such as unilamellar or plurilamellar, so long as the antisense oligonucleotide is contained therein. Positively charged lipids such as N-[1-(2, 3-dioleoyloxi) propyl]-N, N, N- trimethyl- ammoniumethylsulfate, or "DOTAP," are particularly preferred for such particles and vesicles. The preparation of such lipid particles is well known. See, e.g., U.S. Pat. No. 4,880,635 to Janoff et al.; U.S. Pat. No. 4,906,477 to Kurono et al.; U.S. Pat. No. 4,911,928 to Wallach; U.S. Pat. No. 4,917,951 to Wallach; U.S. Pat. No. 4,920,016 to Allen et al.; U.S. Pat. No. 4,921,757 to Wheatley et al.; etc.

The composition of the invention may be administered by any means which transports the antisense nucleotide composition to the lung. The antisense compounds disclosed herein may be administered to the lungs of a patient by any suitable means, but are preferably administered by generating an aerosol comprised of respirable particles, the respirable particles comprised of the antisense compound, which particles the subject inhales. The respirable particles may be liquid or solid, and they may optionally contain other therapeutic ingredients.

Particles comprised of antisense compound for practicing the present invention should be administered as a formulation including particles of respirable size: that is, particles of a size sufficiently small to pass through the nose, mouth and larynx upon inhalation and into the bronchi and alveoli of the lungs. In general, respirable particles range from bout 0.5 to 10 microns in diameter. Particles of non-respirable size which are included in the aerosol tend to deposit in the throat and be swallowed, and the quantity of non-respirable particles in the aerosol is preferably minimized. For nasal administration, a particle size in the range of 10–500 $\mu$m is preferred to ensure retention in the nasal cavity.

Liquid pharmaceutical compositions of active compound for producing an aerosol can be prepared by combining the antisense compound with a suitable vehicle, such as sterile pyrogen free water. Other therapeutic compounds may optionally be included.

Solid particulate compositions containing respirable dry particles of micronized antisense compound may be prepared by grinding dry antisense compound with a mortar and pestle, and then passing the micronized composition through a 400 mesh screen to break up or separate out large agglomerates. A solid particulate composition comprising the antisense compound may optionally contain a dispersant which serves to facilitate the formation of an aerosol. A suitable dispersant is lactose, which may be blended with the antisense compound in any suitable ratio e.g., a 1 to 1 ratio by weight.

The antisense compound may be administered in an amount which depends upon the disease being treated, the condition of the subject, the particular formulation, the route of administration, the timing of administration to a subject, etc. In general, intracellular concentrations of the oligonucleotide of from 0.05 to 50 $\mu$M, or more particularly 0.2 to 5 $\mu$M, are desired. For administration to a subject such as a human, a dosage of from about 0.01, 0.1, or 1 mg/Kg up to 50, 100, or 150 mg/Kg or more is typically employed. Depending on the solubility of the particular formulation of active compound administered, the daily dose may be divided among one or several unit dose administrations. The administration of the antisense compounds may be carried out therapeutically (i.e., as a rescue treatment) or prophylactically.

The aerosols of liquid particles comprising the antisense compound may be produced by any suitable means, such as with a nebulizer. See, e. g., U.S. Pat. No. 4,501,729. Nebulizers are commercially available devices which transform solutions or suspensions of the active ingredient into a therapeutic aerosol mist either by means of acceleration of a compressed gas, typically air or oxygen, through a narrow venturi orifice or by means of ultrasonic agitation. Suitable formulations for use in nebulizers consist of the active ingredient in a liquid carrier, the active ingredient comprising up to 40% w/w, but preferably less than 20% w/w, of the formulation. The carrier is typically water or a dilute aqueous alcoholic solution, preferably made isotonic with body fluids by the addition of, for example, sodium chloride. Optional additives include preservatives if the formulation is not prepared sterile, for example, methyl hydroxybenzoate, antioxidants, flavoring agents, volatile oils, buffering agents and surfactants.

The aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing a predetermined metered dose of a medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder, e.g., a metered dose thereof effective to carry out the treatments described herein, is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation. A second type of illustrative aerosol generator comprises a metered dose inhaler. Metered dose inhalers are pressurized aerosol dispensers, typically containing a suspension or solution formulation of the active ingredient in a liquified propellant. During use these devices discharge the formulation through a valve adapted to deliver a metered volume, typically from 10 to 150 µl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol, surfactants, such as oleic acid or sorbitan trioleate, antioxidants and suitable flavoring agents.

The aerosol, whether formed from solid or liquid particles, may be produced by the aerosol generator at a rate of from about 10 to 150 liters per minute, more preferably from about 30 to 150 liters per minute, and most preferably about 60 liters per minute. Aerosols containing greater amounts of medicament may be administered more rapidly.

The following examples are provided to illustrate the present invention, and should not be construed as limiting thereon. In these examples, $\mu$M means micromolar, mL means milliliters, $\mu$m means micrometers, mm means millimeters, cm means centimeters, °C means degrees Celsius, $\mu$g means micrograms, mg means milligrams, g means grams, kg means kilograms, M means molar, and h means hours.

EXAMPLES

Example 1

Design and synthesis of antisense oligonucleotides

The design of antisense oligonucleotides against the $A_1$ and $A_3$ adenosine receptors may require the solution of the complex secondary structure of the target $A_1$ receptor mRNA and the target $A_3$ receptor mRNA. After generating this structure, antisense nucleotides are designed which target regions of mRNA which might be construed to confer functional activity or stability to the mRNA and which optimally may overlap the initiation codon. Other target sites are readily usable. As a demonstration of specificity of the antisense effect, other oligonucleotides not totally complementary to the target mRNA, but containing identical nucleotide compositions on a w/w basis, are included as controls in antisense experiments.

Adenosine $A_1$ receptor mRNA secondary structure was analyzed and used as described above to design a phosphorothioate antisense oligonucleotide. The antisense oligonucleotide which was synthesized was designated HAdA1AS and had the following sequence:

5'-GAT GGA GGG CGG CAT GGC GGG-3' (SEQ ID NO:1)

As a control, a mismatched phosphorothioate antisense nucleotide designated HAdA1MM was synthesized with the following sequence:

5'-GTA GCA GGC GGG GAT GGG GGC-3' (SEQ ID NO:2)

Each oligonucleotide had identical base content and general sequence structure. Homology searches in GENBANK (release 85.0) and EMBL (release 40.0) indicated that the antisense oligonucleotide was specific for the human and rabbit adenosine $A_1$ receptor genes, and that the mismatched control was not a candidate for hybridization with any known gene sequence.

Adenosine $A_3$ receptor mRNA secondary structure was similarly analyzed and used as described above to design two phosphorothioate antisense oligonucleotides. The first antisense oligonucleotide (HAdA3AS1) synthesized had the following sequence:

5'-GTT GTT GGG CAT CTT GCC-3' (SEQ ID NO:3)

As a control, a mismatched phosphorothioate antisense oligonucleotide (HAdA3MM1) was synthesized, having the following sequence:

5'-GTA CTT GCG GAT CTA GGC-3' (SEQ ID NO:4)

A second phosphorothioate antisense oligonucleotide (HAdA3AS2) was also designed and synthesized, having the following sequence:

5'-GTG GGC CTA GCT CTC GCC-3' (SEQ ID NO:5)

Its control oligonucleotide (HAdA3MM2) had the sequence:

5'-GTC GGG GTA CCT GTC GGC-3' (SEQ ID NO:6)

Phosphorothioate oligonucleotides were synthesized on an Applied Biosystems Model 396 Oligonucleotide Synthesizer, and purified using NENSORB chromatography (DuPont, Md.).

Example 2

Testing of A1-Adenosine Receptor Antisense Oligonucleotides in vitro

The antisense oligonucleotide against the human $A_1$ receptor (SEQ ID NO:1) described above was tested for efficacy in an in vitro model utilizing lung adenocarcinoma cells HTB-54. HTB-54 lung adenocarcinoma cells were demonstrated to express the $A_1$ adenosine receptor using standard northern blotting procedures and receptor probes designed and synthesized in the laboratory.

HTB-54 human lung adenocarcinoma cells (106/100 mm tissue culture dish) were exposed to 5.0 $\mu$M HAdA1AS or HAdA1MM for 24 hours, with a fresh change of media and oligonucleotides after 12 hours of incubation. Following 24 hour exposure to the oligonucleotides, cells were harvested and their RNA extracted by standard procedures. A 21-mer probe corresponding to the region of mRNA targeted by the antisense (and therefore having the same sequence as the antisense, but not phosphorothioated) was synthesized and used to probe northern blots of RNA prepared from HAdA1AS-treated, HAdA1MM-treated and non-treated HTB-54 cells. These blots showed clearly that HAdA1AS but not HAdA1MM effectively reduced human adenosine receptor mRNA by >50%. This result showed that HAdA1AS is a good candidate for an anti-asthma drug since it depletes intracellular mRNA for the adenosine $A_1$ receptor, which is involved in asthma.

Example 3

Efficacy of $A_1$-Adenosine Receptor Antisense Oligonucleotides in vivo

A fortuitous homology between the rabbit and human DNA sequences within the adenosine $A_1$ gene overlapping the initiation codon permitted the use of the phosphorothioate antisense oligonucleotides initially designed for use against the human adenosine $A_1$ receptor in a rabbit model.

Neonatal New Zealand white Pasteurella-free rabbits were immunized intraperitoneally within 24 hours of birth with 312 antigen units/mL house dustmite (*D. farinae*) extract (Berkeley Biologicals, Berkeley, Calif.), mixed with 10% kaolin. Immunizations were repeated weekly for the first month and then biweekly for the next 2 months. At 3–4 months of age, eight sensitized rabbits were anesthetized and relaxed with a mixture of ketamine hydrochloride (44 mg/kg) and acepromazine maleate (0.4 mg/kg) administered intramuscularly.

The rabbits were then laid supine in a comfortable position on a small molded, padded animal board and intubated with a 4.0 -mm intratracheal tube (Mallinkrodt, Inc., Glens Falls, N.Y.). A polyethylene catheter of external diameter 2.4 mm with an attached latex balloon was passed into the esophagus and maintained at the same distance (approximately 16 cm) from the mouth throughout the experiments. The intratracheal tube was attached to a heated Fleisch pneumotachograph (size 00; DOM Medical, Richmond, Va.), and flow was measured using a Validyne differential pressure transducer (Model DP-45161927; Validyne Engineering Corp., Northridge, Calif.) driven by a Gould carrier amplifier (Model 11-4113; Gould Electronic, Cleveland, Ohio). The esophageal balloon was attached to one side of the differential pressure transducer, and the outflow of the intratracheal tube was connected to the opposite side of the pressure transducer to allow recording of transpulmonary pressure. Flow was integrated to give a continuous tidal volume, and measurements of total lung resistance (RL) and dynamic compliance (Cdyn) were calculated at isovolumetric and flow zero points, respectively, using an automated respiratory analyzer (Model 6; Buxco, Sharon, Conn.).

Animals were randomized and on Day 1 pretreatment values for. PC50 were obtained for aerosolized adenosine. Antisense (HAdA1AS) or mismatched control (HAdA1MM) oligonucleotides were dissolved in sterile physiological saline at a concentration of 5000 ug (5 mg) per 1.0 ml. Animals were subsequently administered the aerosolized antisense or mismatch oligonucleotide via the intratracheal tube (approximately 5000 µg in a volume of 1.0 ml), twice daily for two days. Aerosols of either saline, adenosine, or antisense or mismatch oligonucleotides were generated by an ultrasonic nebulizer (DeVilbiliss, Somerset, Pa.), producing aerosol droplets 80% of which were smaller than 5 µm in diameter.

In the first arm of the experiment, four randomly selected allergic rabbits were administered antisense oligonucleotide and four the mismatched control oligonucleotide. On the morning of the third day, PC50 values (the concentration of aerosolized adenosine in mg/ml required to reduce the dynamic compliance of the bronchial airway 50% from the baseline value) were obtained and compared to PC50 values obtained for these animals prior to exposure to oligonucleotide.

Following a 1 week interval, animals were crossed over, with those previously administered mismatch control oligonucleotide now administered antisense oligonucleotide, and those previously treated with antisense oligonucleotide now administered mismatch control oligonucleotide. Treatment methods and measurements were identical to those employed in the first arm of the experiment. It should be noted that in six of the eight animals treated with antisense oligonucleotide, adenosine-induced bronchoconstriction could not be obtained up to the limit of solubility of adenosine, 20 mg/ml. For the purpose of calculation, PC50 values for these animals were set at 20 mg/ml. The values given therefore represent a minimum figure for antisense effectiveness. Actual effectiveness was higher. The results of this experiment are illustrated in both FIG. 1 and Table 1.

TABLE 1

EFFECTS OF ADENOSINE $A_1$ RECEPTOR ANTISENSE OLIGONUCLEOTIDE UPON PC50 VALUES IN ASTHMATIC RABBITS.

| Mismatch Control | | $A_1$ receptor Antisense oligonucleotide | |
|---|---|---|---|
| Pre oligonucleotide | Post oligonucleotide | Pre oligonucleotide | Post oligonucleotide |
| 3.56 ± 1.02 | 5.16 ± 1.93 | 2.36 ± 0.68 | >19.5 ± 0.34** |

Results are presented as the mean (N = 8) ± SEM. Significance was determined by repeated-measures analysis of variance (ANOVA), and Tukey's protected t test. **Significantly different from all other groups, $P < 0.01$.

In both arms of the experiment, animals receiving the antisense oligonucleotide showed an order of magnitude increase in the dose of aerosolized adenosine required to reduce dynamic compliance of the lung by 50%. No effect of the mismatched control oligonucleotide upon PC50 values was observed. No toxicity was observed in any animal receiving either antisense or control inhaled oligonucleotide.

These results show clearly that the lung has exceptional potential as a target for antisense oligonucleotide-based therapeutic intervention in lung disease. They further show, in a model system which closely resembles human asthma, that downregulation of the adenosine $A_1$ receptor largely eliminates adenosine-induced bronchoconstriction in asthmatic airways. Bronchial hyperresponsiveness in the allergic rabbit model of human asthma is an excellent endpoint for antisense intervention since the tissues involved in this response lie near to the point of contact with aerosolized oligonucleotides, and the model closely simulates an important human disease.

Example 4

Specificity of $A_1$-adenosine receptor Antisense oligonucleotide

At the conclusion of the crossover experiment of Example 3, airway muscle from all rabbits was quantitatively analyzed for adenosine $A_1$ receptor number. As a control for the specificity of the antisense oligonucleotide, adenosine $A_2$ receptors, which should not have been affected, were also quantified.

Airway smooth muscle tissue was dissected from each rabbit and a membrane fraction prepared according to described methods (J. Kleinstein and H. Glossmann, *Naunyn-Schmiedeberg's Arch. Pharmacol.* 305, 191–200 (1978), with slight modifications. Crude plasma membrane preparations were stored at −70° C. until the time of assay. Protein content was determined by the method of Bradford (M. Bradford, *Anal. Biochem.* 72, 240–254 (1976)). Frozen plasma membranes were thawed at room temperature and were incubated with 0.2 U/ml adenosine deaminase for 30 minutes at 37° C. to remove endogenous adenosine. The binding of [$^3$H]DPCPX ($A_1$ receptor-specific) or [$^3$H]CGS-21680 ($A_2$ receptor-specific) was measured as previously described. S. Ali et al., *J. Pharmacol. Exp. Ther.* 268, 1328–1334 (1994); S. Ali et al., *Am. J. Physiol* 266, L271–277 (1994).

Figure 2:
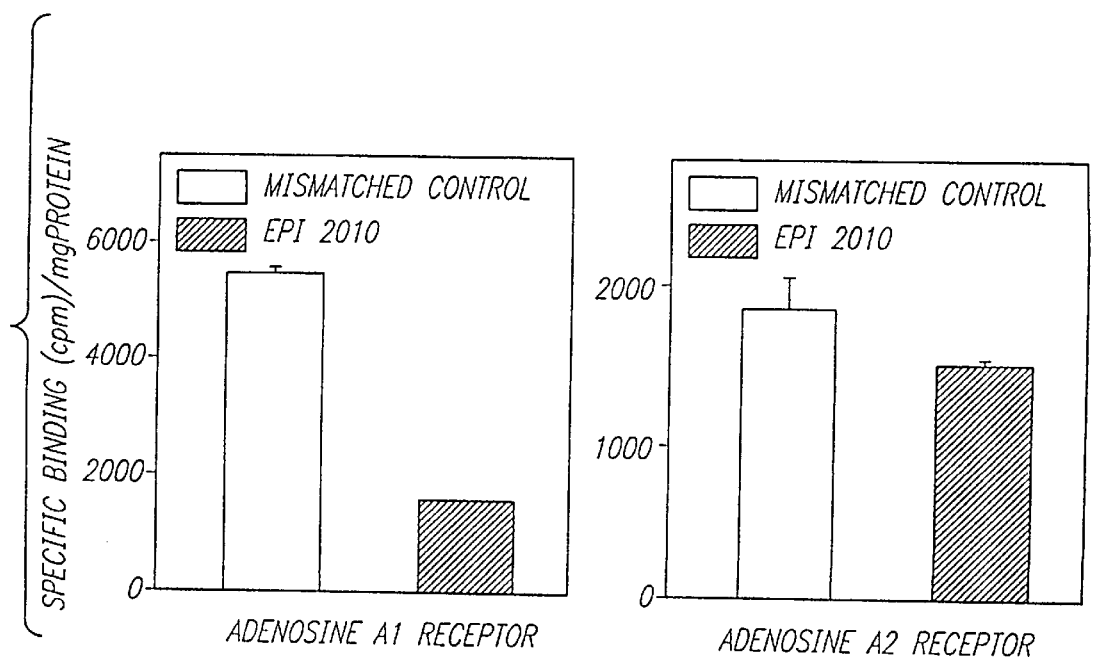

As illustrated in both FIG. 2 and Table 2, animals treated with adenosine $A_1$ antisense oligonucleotide in the crossover experiment had a nearly 75% decrease in $A_1$ receptor number compared to controls, as assayed by specific binding of the $A_1$-specific antagonist DPCPX. There was no change in adenosine $A_2$ receptor number, as assayed by specific binding of the $A_2$ receptor-specific agonist 2-[p-(2-carboxyethyl)-phenethylamino]-5'-(N-ethylcarboxamido) adenosine (CGS-21680).

TABLE 2

SPECIFICITY OF ACTION OF ADENOSINE $A_1$ RECEPTOR ANTISENSE OLIGONUCLEOTIDE.

|  | Mismatch Control oligonucleotide | $A_1$ Antisense oligonucleotide |
|---|---|---|
| $A_1$-Specific Binding | 1105 ± 48** | 293 ± 18 |
| $A_2$-Specific Binding | 302 ± 22 | 442 ± 171 |

Results are presented as the mean (N = 8) ± SEM. Significance was determined by repeated-measures analysis of variance (ANOVA), and Tukey's protected t test. **Significantly different from mismatch control, P < 0.01.

The above demonstrates the effectiveness of antisense oligonucleotides in treating airway diseases. Since the antisense oligonucleotides described above eliminate the receptor systems responsible for adenosine-mediated bronchoconstriction, it may be less imperative to eliminate adenosine from them. However, it would be preferable to eliminate adenosine from even these oligonucleotides. Described below is a series of antisense oligonucleotides targetting mRNA of proteins involved in inflammation. Adenosine has been eliminated from their nucleotide content to prevent its liberation during degradation.

Example 5

The method of the present invention is also practiced with the following antisense oligonucleotides targeted to their corresponding proteins, in essentially the same manner as given above, for the treatment of various conditions in the lungs:

```
Human A2a adenosine receptor:
        TGCTTTTCTT TTCTGGGCCT C                          (SEQ ID NO:7)

Human A2b adenosine receptor:
        GGCGCCGTGC CGCGTCTTGG  TGGCGGCGG                 (SEQ ID NO:8)

Human IgE receptor β:
        TTTCCCCTGG GTCTTCC                               (SEQ ID NO:9)

Human Fc-epsilon receptor CD23 antigen (IgE receptor):
        GCCTGTGTCT CTCCTCCT                              (SEQ ID NO:10)

Human IgE receptor, α subunit:
        GCCTTTCCTG GTTCTCTT                              (SEQ ID NO:11)

Human IgE receptor, Fc epsilon R:
        GCCTGTGTCT GTCCTCCT                              (SEQ ID NO:12)

Human histidine decarboxylase:
        TCTCCCTTGG GCTCTGGCTC CTTCTC                     (SEQ ID NO:13)

Human beta tryptase:
        CTTGCTCCTG GGGGCCTCCT G                          (SEQ ID NO:14)

Human tryptase-I:
        CTTGCTCCTG GGGGCCTCCT G                          (SEQ ID NO:15)

Human prostaglandin D synthase:
        GGTGTGCGGG GCCTGGTGCC                            (SEQ ID NO:16)

Human cyclooxygenase-2:
        GGGCGCGGGC GAGCATCGC                             (SEQ ID NO:17)

Human eosinophil cationic protein:
        CCTCCTTCCT GGTCTGTCTG C                          (SEQ ID NO:18)

Human eosinophil derived neurotoxin:
        GCCCTGCTGC TCTTTCTGCT                            (SEQ ID NO:19)

Human eosinophil peroxidase:
        GCGCTCGGCC TGGTCCCGG                             (SEQ ID NO:20)

Human intercellular adhesion molecule-1 (CAM-1):
        GCGCGGGCCG GGGGCTGCTG GG                         (SEQ ID NO:21)

Human vascular cell adhesion molecule 1 (VCAM-1):
        CCTCTTTTCT GTTTTTCCC                             (SEQ ID NO:22)

Human endothelial leukocyte adhesion molecule (ELAM-1):
        GTTCTTGGCT TCTTCTGTC                             (SEQ ID NO:23)
```

-continued

Human P Selectin:
    CTCTGCTGGT TTTCTGCCTT CTGCCC                          (SEQ ID NO:24)

Human endothelial monocyte activating factor:
    TTTTCTCTTT CGCTTTCTTT TCGTCTCCTG TTCCTCCTTT T         (SEQ ID NO:25)

Human IL3:
    CTCTGTCTTG TTCTGGTCCT TCGTGGGGCT CTG                  (SEQ ID NO:26)

Human IL4:
    CTCTGGTTGG CTTCCTTC                                   (SEQ ID NO:27)

Human IL5:
    TCCCTGTTTC CCCCCTTT                                   (SEQ ID NO:28)

Human IL6:
    GCTTCTCTTT CGTTCCCGGT GGGCTCG                         (SEQ ID NO:29)

Human monocyte-derived neutrophil chemotactic factor:
    GCTTGTGTGC TCTGCTGTCT CT                              (SEQ ID NO:30)

Human neutrophil elastase (medullasin):
    TGGTGGGGCT GGGGCTCCGG GGTCTCTGCC CCTCCGTGC            (SEQ ID NO:31)

Human neutrophil oxidase factor:
    GTCCTTCTTG TCCGCTGCC                                  (SEQ ID NO:32)

Human cathepsin G:
    GTGGGGCCTG CTCTCCCGGC CTCCG                           (SEQ ID NO:33)

Human defensin 1:
    GGGTCCTCAT GGCTGGGG                                   (SEQ ID NO:34)

Human defensin 3:
    GGGTCCTCAT GGCTGGGGTC                                 (SEQ ID NO:35)

Human macrophage inflammatory protein-1-alpha:
    GTCTTTGTTT CTGGGCTCGT GCC                             (SEQ ID NO:36)

Human muscarinic acetylcholine receptor HM1:
    GTTCATGGTG GCTAGGTGGG GC                              (SEQ ID NO:37)

Human muscarinic acetylcholine receptor HM3:
    GGGGTGGGTA GGCCGTGTCT GGGG                            (SEQ ID NO:38)

Human fibronectin:
    CGGTTTCCTT TGCGGTC                                    (SEQ ID NO:39)

Human interleukin 8:
    GTGCTCCGGT GGCTTTTT                                   (SEQ ID NO:40)

Human GM-CSF:
    GGTCCAGCCA TGGGTCTGGG                                 (SEQ ID NO:41)

Human tumor necrosis factor α:
    GCTGGTCCTC TGCTGTCCTT GCTG                            (SEQ ID NO:42)

Human leukotriene C4 synthase:
    GCCCCGTCTG CTGCTCCTCG TGCCG                           (SEQ ID NO:43)

Human major basic protein:
    GTTTCATCTT GGCTTTATCC                                 (SEQ ID NO:44)

The foregoing examples are illustrative of the present invention, and are not to be construed as limiting thereof.

The invention is defined by the following claims, with equivalents of the claims to be included therein.

---

That which is claimed is:

1. A pharmaceutical composition, comprising
an oligonucleotide (oligo) in aerosol form, which is effective for aleviating bronchoconstriction or lung inflammation when administered to a mammal; wherein the oligo contains no more than 3 adenosines (A) or, if at least 21 nucleotides long, it contains no more than 3 per every 21 nucleouides; and
is antisense to the initiation codon, the coding region or the 5' or 3' intron-exon junctions of a gene encoding an adenosine $A_1$ receptor, adenosine $A_{2a}$ receptor, adenosine $A_{2b}$ receptor, or adenosine $A_3$ receptor, or anti-sense to their respective mRNAs; and
a pharmaceutically acceptable carrier.

2. The composition of claim 1, wherein the oligo comprises at least one mononucleotide linking residue selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamnide, sulfone, sulfite, sulfoxide, sulfide, hydroxylamine, methylene(methyimino), methyleneoxy (methylimino) and phosphoramidate residues.

3. The composition of claim 2, wherein all mononucleotide linking residues of the oligo are selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene(methyimino), methyleneoxy (methylimino) and phosphoramidate residues.

4. The composition of claim 3, wherein all nucleotide linking residues are phosphorothioates.

5. The composition of claim 1, wherein the oligo is antisense to the initiation codon, the coding region or the 5' or 3' intron-exon junctions of a gene encoding an adenosine $A_1$ receptor or anti-sense to its mRNA.

6. The composition of claim 5, wherein all nucleotide linking residues are phosphorothioates.

7. The composition of claim 1, wherein the oligo is antisense to the initiation codon, the coding region or the 5' or 3' intron-exon junctions of a gene encoding an adenosine $A_{2a}$ receptor or anti-sense to its mRNA.

8. The composition of claim 7, wherein all nucleotide linking residues are phosphorothioates.

9. The composition of claim 1, wherein the oligo is antisense to the initiation codon, the coding region or the 5' or 3' intron-exon junctions of a gene encoding an adenosine $A_{2b}$ receptor or anti-sense to its mRNA.

10. The composition of claim 9, wherein all nucleotide linking residues are phosphorothioates.

11. The composition of claim 1, wherein the oligo is antisense to the initiation codon, the coding region or the 5' or 3' intron-exon junctions of a gene encoding an adenosine $A_3$ receptor or anti-sense to its mRNA.

12. The composition of claim 11, wherein all nucleotide linking residues are phosphorothioates.

13. The composition of claim 1, wherein the oligo is a DNA.

14. The composition of claim 1, wherein the oligo is an RNA.

15. The composition of claim 1, wherein the oligo comprises about 10 to up to about 60 mononucleotides.

16. The composition of claim 1, wherein the oligo comprises about 18 up to about 21 mononucleotides.

17. The composition of claim 1, wherein the oligo consists of
SEQ ID NO.: 7; or
SEQ ID NO.: 7; wherein at least one mononucleotide linking residue is selected from the group consisting of methylphosphonate, phosphotriester, phosphorothioate, phosphorodithioate, boranophosphate, formacetal, thioformacetal, thioether, carbonate, carbamate, sulfate, sulfonate, sulfaimate, sulfonamide, sulfone, sulfite, sulfoxide, sulfide, hydroxylarnine, methylene(methyimino), methyleneoxy (methylimino) and phosphoramidate residues.

18. The composition of claim 17, wherein all nucleotide linking residues are phosphorothioates.

19. The composition of claim 1, wherein the oligo consists of
SEQ ID NO.: 8; or
SEQ ID NO.: 8; wherein at least one mononucleotide linking residue is selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonarmide, sulfone, sulfite, sulfoxide, sulfide, hydroxylamine, methylene(methyimino), methyleneoxy (methylimino) and phosphoramidate residues.

20. The composition of claim 19, wherein all nucleotide linking residues are phosphorothioates.

21. The composition of claim 1, wherein the oligo is linked to a molecule selected from the group consisting of transferrin, asialoglycoprotein and streptavidin.

22. The composition of claim 1, wherein the oligo is at least 18 nucleotides long and contains no more than 1 adenosine per every 18 nucleotide.

23. The composition of claim 1, wherein the oligo is an adenosine-free oligo.

24. The composition of claim 1, further comprising an agent selected from the group consisting of antioxidants, surfactants, flavoring agents, volatile oils, buffering agents, dispersants, propellants and preservatives.

25. The composition of claim 1, wherein said pharmaceutical composition is prepared for dispensing from a pressurized aerosol dispenser.

26. The composition of claim 1, wherein said pharmaceutical composition is prepared for dispensing from a metered dose inhaler.

27. The composition of claim 1, wherein the carrier is selected from the group consisting of solid and liquid carriers.

28. The composition of claim 27, wherein the aerosol comprises a solution or suspension of the oligo.

29. The composition of claim 26, wherein said pharmaceutical composition is in the form of a spray.

30. The composition of claim 29, further comprising a buffer and a further agent selected from the group consisting of antioxidants, surfactants, flavoring agents, volatile oils, buffering agents, dispersants, propellants and preservatives.

31. The composition of claim 29, which is a respirable formulation, wherein the carrier is a respirable carrier, and which may further comprise an agent selected from the group consisting of antioxidants, flavoring agents, volatile oils, buffering agents, dispersants, surfactants, propellants and preservatives.

32. The respirable composition of claim 31, wherein at least one of the mononucleotide linking residues of the oligo is selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene(methyimino), methyleneoxy (methylimino) and phosphoramidate residues.

33. The composition of claim 1, wherein the oligo is present in an amount of about 0.1 to about 100% w/w of the composition.

34. The composition of claim 33, wherein the oligo is present in an amount of about 0.1 to about 40% w/w of the composition.

35. The composition of claim 34, wherein the oligo is present in an amount of about 0.1 up to about 20% w/w of the composition.

36. The composition of claim 1, wherein the carrier comprises a hydrophobic carrier.

37. The composition of claim 36, wherein the carrier comprises lipid particles or vesicles.

38. The composition of claim 37, wherein the vesicles comprise liposomes and the particles comprise microcrystals.

39. The composition of claim 37, wherein the vesicles comprise liposomes which comprise the antisense oligo.

40. The composition of claim 37, wherein the particles comprise a lipid selected from the group consisting of N-(1-(2, 3-dioleoxyloxi) propyl)-N, N, N-trimethyl-ammoniummethylsulfate.

41. The composition of claim 1, comprised in a capsule or cartridge.

42. The composition of claim 1, comprising solid or liquid particles of the oligo.

43. The composition of claim 1, comprising a suspension or solution of the oligo.

44. The composition of claim 43, wherein the oligo is suspended or dissolved in a solvent or mixture of solvents.

45. The composition of claim 44, wherein the solvent is chlorofluorocarbons or chlorofluorocarbons with co-solvents, and the pharmaceutical composition further comprises an agent selected from the group consising of surfactants, antioxidants and flavoring agents.

46. The composition of claim 1, further comprising a surfactant.

47. A method of treating an adenosine receptor mediated respiratory disease or condition associated with bronchoconstriction or lung inflammation, comprising administering directly to the respiration of a mammalian subject in need of such treatment the pharmaceutical composition of claim 1, comprising an amount of the oligo effective for alleviating bronchoconstriction and/or lung inflammation.

48. The method of claim 47, wherein the pharmaceutical composition comprises respirable particles comprising the oligo.

49. The method of claim 47, wherein the disease or condition comprises lung inflammation.

50. The method of claim 47, wherein the disease or condition comprises a disease or condition asociated with bronchoconstriction.

51. The method of claim 47, wherein the disease or condition comprises asthma.

52. The method of claim 47, wherein the mammalian subject is non-human.

53. The method of clam 47, wherein the mammalian subject is a human.

54. The method of claim 47, wherein the oligo is administered in an amount of about 0.01 to about 150 mg/kg body weight.

55. The method of claim 54, wherein the oligo is administered in an amount of about 1 to about 100 mg/kg body weight.

56. The method of claim 55, wherein the oligo is administered in an amount of about 10 up to about 50 mg/kg body weight.

57. The method of claim 47, being a prophylactic method.

58. The method of claim 47, being a therapeutic method.

59. The method of claim 47, wherein the pharmaceutical composition further comprises an agent selected from the group consisting of antioxidants, flavoring agents, volatile oils, buffering agents, dispersants, surfactants, propellants and preservatives.

60. The method of claim 47, wherein the oligo is antisense to the coding region or the initiation codon of a gene encoding the adenosine receptor or antisense to an adenosine receptor mRNA; wherein at least one mononucleotide linking residue is selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene(methyimino), methyleneoxy (methylimino) and phosphoramidate residues.

61. The method of claim 60, wherein all mononucleotide linking residues of the oligo are selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene(methyimino), methyleneoxy (methylimino) and phosphoramidate residues.

62. The method of claim 61, wherein the pharmaceutical composition further comprises a surfactant.

63. The method of claim 47, wherein the oligo is

SEQ. ID NO:7; or

SEQ. ID NO:7, wherein at least one mononucleotide linking residue is selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene(methyimino), methyleneoxy (methylimino) and phosphoramidate residues.

64. The method of claim 63, wherein the oligo is SEQ. ID NO:7, wherein all mononucleotide linking residues are selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene(methyimino), methyleneoxy (methylimino) and phosphoramidate residues.

65. The method of claim 64, wherein all mononucleotide linking residues are phosphorothioate residues.

66. The method of claim 63, wherein the oligo is selected from

SEQ. ID NO: 8; or

SEQ. ID NO: 8, wherein at least one mononucleotide linking residue is selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene(methyimino), methyleneoxy (methylimino) and phosphoramidate residues.

67. The method of claim 66, wherein all mononucleotide linking residues are selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene(methyimino), methyleneoxy (methylimino) and phosphoramidate residues.

68. The method of claim 67, wherein all mononucleotide linking residues are phosphorothioates.

69. An in vivo method of delivering an oligonucleotide (oligo) to a target adenosine receptor polynucleotide, comprising administering into a mammalian subject's respiration an aerosol of the composition of claim 1, comprising an amount of the adenosine receptor oligo effective to reach the target adenosine receptor polynucleotide.

70. The method of claim 69, wherein the aerosol comprises respirable oligo particles.

71. The method of claim 69, wherein the oligo is oligos which are antisense to an intron-exon junction of an adenosine receptor gene selected from the group consisting of adenosine A1, A2a, A2b and A3 receptors or antisense to the corresponding adenosine receptor mRNA; or oligos which are antisense to an intron-exon junction of an adenosine receptor gene selected from the group consisting of adenosine A1, A2a, A2b and A3 receptors or antisense to the corresponding adenosine receptor mRNA, wherein the oligo comprises at least one mononucleotide linking residue selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene(methyimino), methyleneoxy (methylimino) and phosphoramidate residues.

72. The method of claim 69, wherein the oligo is delivered to alleviate a disease or condition associated with bronchoconstriction.

73. The method of claim 72, wherein the disease or condition comprises asthma.

74. The method of claim 69, wherein the mammalian subject is a human.

75. The method of claim 69, wherein the mammalian subject is an non-human mammal.

76. The method of claim 69, wherein the oligo is administered in an amount of about 0.01 to about 150 mg/kg body weight.

77. The method of claim 76, wherein the oligo is administered in an amount of about 1 to about 100 mg/kg body weight.

78. The method of claim 77, wherein the oligo is administered in an amount of about 1 up to about 50 mg/kg body weight.

79. The method of claim 69, being a prophylactic method.

80. The method of claim 69, being a therapeutic method.

81. The method of claim 69, wherein the composition further comprises an agent selected from the group consisting of antioxidants, flavoring agents, volatile oils, buffering agents, dispersants, surfactants, propellants and preservatives.

82. The method of claim 81, wherein the composition further comprises a surfactant.

83. The method of claim 69, wherein the oligo is SEQ. ID NO: 7, and at least one mononucleotide linking residue is selected from the group consisting of methylphosphonate, phosphotriester, phosphorothioate, phosphorodithioate, boranophosphate, formacetal, thioformacetal, thioether, carbonate, carbamate, sulfate, sulfonate, sulfarnate, sulfonamide, sulfone, sulfite, sulfoxide, sulfide, hydroxylamine, methylene (methyimino), methyleneoxy (methylimino) and phosphoramidate residues.

84. The method of claim 83, wherein all mononucleotide linking residues are selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene (methyimino), methyleneoxy (methylimino) and phosphoramidate residues.

85. The method of claim 84, wherein all mononucleotide linking residues are phosphorothioates.

86. The method of claim 69, wherein the oligo is SEQ. ID NO: 8, wherein at least one mononucleotide linking residue is selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene (methyimino), methyleneoxy (methylimino) and phosphoramidate residues.

87. The method of claim 86, wherein all mononucleotide linking residues are selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene (methyimino), methyleneoxy (methylimino) and phosphoramidate residues.

88. The method of claim 87, wherein all mononucleotide linking residues are phosphorothioates.

89. The method of claim 69, wherein the oligo is oligos which are antisense to the coding region of a gene encoding an adenosine receptor selected from the group consisting of adenosine A1, A2a, A2b and A3 receptors, or antisense to the corresponding adenosine receptor mRNA; or oligos which are antisense to the coding region of a gene encoding an adenosine receptor selected from the group consisting of adenosine A1, A2a, A2b and A3 receptors, or antisense to the corresponding adenosine receptor mRNA, wherein at least one mononucleotide linking residue is selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene (methyimino), methyleneoxy (methylimino) and phosphoramidate residues.

90. A method of alleviating an airway disease or condition associated with adenosine receptor mediated bronchoconstriction or lung inflammation, comprising conducting the method of claim 89, by administering a bronchoconstriction or lung inflammation reducing amount of the oligo.

91. The method of claim 90, wherein the amount of oligo administered is effective to reduce either the level of the mRNA encoding the polypeptide or of the mRNA-encoded polypeptide, or to effect beneficial changes in the growth or characteristics of lung cells.

92. The method of claim 69, wherein the composition is dispensed from a pressurized aerosol dispenser.

93. The method of claim 69, wherein the composition is dispensed from a metered dose inhaler.

94. The method of claim 90, wherein the airway disease is associated with bronchoconstriction.

95. The method of claim 90, wherein the airway disease is associated with inflammation.

96. The method of claim 90, wherein the airway disease is associated with asthma.

97. The method of claim 90, wherein the subject is a mammal.

98. The method of claim 97, wherein the mammal is a non-human mammal.

99. The method of claim 97, wherein the mammal is a human.

100. The method of claim 90, wherein the agent is administered in an amount of about 0.01 to about 150 mg/kg body weight.

101. The method of claim 90, which is a prophylactic method.

102. The method of claim 90, which is a therapeutic method.

103. The method of claim 47, wherein the disease or condition comprises a disease or condition associated with lung inflammation.

104. The method of claim 71, wherein all the mononucleotide linking residues are selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene (methyirmino), methyleneoxy (methylimino) and phosphoramidate residues.

105. The method of claim 69, wherein the oligo is delivered to alleviate a disease or condition associated with lung inflammation.

* * * * *

SEQUENCE LISTING (1) GENERAL INFORMATION:

(iii) NUMBER OF SEQUENCES: 44

(2) INFORMATION FOR SEQ ID NO:1:

(i) SEQUENCE CHARACTERISTICS:

```
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

GATGGAGGGC GGCATGGCGG G                                              21

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

GTAGCAGGCG GGGATGGGGG C                                              21

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GTTGTTGGGC ATCTTGCC                                                  18

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GTACTTGCGG ATCTAGGC                                                  18

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GTGGGCCTAG CTCTCGCC                                                  18

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear
```

-continued (ii) MOLECULE TYPE: DNA (genomic)

(xi) SEQUENCE DESCRIPTION: SEQ ID NO:6:

GTCGGGGTAC CTGTCGGC                                            18

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TGCTTTTCTT TTCTGGGCCT C                                        21

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GGCGCCGTGC CGCGTCTTGG TGGCGGCGG                                29

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

TTTCCCCTGG GTCTTCC                                             17

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GCCTGTGTCT CTCCTCCT                                            18

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GCCTTTCCTG GTTCTCTT                                            18

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GCCTGTGTCT GTCCTCCT                                                  18

(2) INFORMATION FOR SEQ ID NO:13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

TCTCCCTTGG GCTCTGGCTC CTTCTC                                    26

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CTTGCTCCTG GGGGCCTCCT G                                           21

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

CTTGCTCCTG GGGGCCTCCT G                                           21

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GGTGTGCGGG GCCTGGTGCC                                           20

(2) INFORMATION FOR SEQ ID NO:17:

(i) SEQUENCE CHARACTERISTICS:

(A) LENGTH: 19 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 12
        (D) OTHER INFORMATION: /standard_name= "Reduced A"

(ix) FEATURE:
        (A) NAME/KEY: misc_feature
        (B) LOCATION: 15
        (D) OTHER INFORMATION: /standard_name= "Reduced A"

(xi) SEQUENCE DESCRIPTION: SEQ ID NO:17:

GGGCGCGGGC GAGCATCGC                                                        19

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

CCTCCTTCCT GGTCTGTCTG C                                                     21

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

GCCCTGCTGC TCTTTCTGCT                                                       20

(2) INFORMATION FOR SEQ ID NO:20:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GCGCTCGGCC TGGTCCCGG                                                        19

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

GCGCGGGCCG GGGGCTGCTG GG                                                    22

(2) INFORMATION FOR SEQ ID NO:22:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

CCTCTTTTCT GTTTTTCCC                                                        19

(2) INFORMATION FOR SEQ ID NO:23:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

GTTCTTGGCT TCTTCTGTC                                                        19

(2) INFORMATION FOR SEQ ID NO:24:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

CTCTGCTGGT TTTCTGCCTT CTGCCC                                         26

(2) INFORMATION FOR SEQ ID NO:25:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

TTTTCTCTTT CGCTTTCTTT TCGTCTCCTG TTCCTCCTTT T                    41

(2) INFORMATION FOR SEQ ID NO:26:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

CTCTGTCTTG TTCTGGTCCT TCGTGGGGCT CTG                                33

(2) INFORMATION FOR SEQ ID NO:27:

(i) SEQUENCE CHARACTERISTICS:

```
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

CTCTGGTTGG CTTCCTTC                                              18

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

TCCCTGTTTC CCCCCTTT                                              18

(2) INFORMATION FOR SEQ ID NO:29:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

GCTTCTCTTT CGTTCCCGGT GGGCTCG                                    27

(2) INFORMATION FOR SEQ ID NO:30:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

GCTTGTGTGC TCTGCTGTCT CT                                         22

(2) INFORMATION FOR SEQ ID NO:31:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

TGGTGGGGCT GGGGCTCCGG GGTCTCTGCC CCTCCGTGC                       39

(2) INFORMATION FOR SEQ ID NO:32:

(i) SEQUENCE CHARACTERISTICS:
        (A) LENGTH: 19 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:32:

GTCCTTCTTG TCCGCTGCC                                                    19

(2) INFORMATION FOR SEQ ID NO:33:

(i) SEQUENCE CHARACTERISTICS:
           (A) LENGTH: 25 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:33:

GTGGGGCCTG CTCTCCCGGC CTCCG                                             25

(2) INFORMATION FOR SEQ ID NO:34:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:34:

GGGTCCTCAT GGCTGGGG                                                     18

(2) INFORMATION FOR SEQ ID NO:35:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: DNA (genomic)

(ix) FEATURE:
           (A) NAME/KEY: misc_feature
           (B) LOCATION: 9
           (D) OTHER INFORMATION: /standard_name= "Reduced A"

(xi) SEQUENCE DESCRIPTION: SEQ ID NO:35:

GGGTCCTCAT GGCTGGGGTC                                                   20

(2) INFORMATION FOR SEQ ID NO:36:

(i) SEQUENCE CHARACTERISTICS:
           (A) LENGTH: 23 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:36:

GTCTTTGTTT CTGGGCTCGT GCC                                               23

(2) INFORMATION FOR SEQ ID NO:37:

(i) SEQUENCE CHARACTERISTICS:
           (A) LENGTH: 22 base pairs
           (B) TYPE: nucleic acid
           (C) STRANDEDNESS: single
           (D) TOPOLOGY: linear

```
    (ii) MOLECULE TYPE: DNA (genomic)

(ix) FEATURE:
         (A) NAME/KEY: misc_feature
         (B) LOCATION: 5
         (D) OTHER INFORMATION: /standard_name= "Reduced A"

(ix) FEATURE:
         (A) NAME/KEY: misc_feature
         (B) LOCATION: 14
         (D) OTHER INFORMATION: /standard_name= "Redcued A"

(xi) SEQUENCE DESCRIPTION: SEQ ID NO:37:

GTTCATGGTG GCTAGGTGGG GC                                            22

(2) INFORMATION FOR SEQ ID NO:38:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ix) FEATURE:
         (A) NAME/KEY: misc_feature
         (B) LOCATION: 10
         (D) OTHER INFORMATION: /standard_name= "Reduced A"

(xi) SEQUENCE DESCRIPTION: SEQ ID NO:38:

GGGGTGGGTA GGCCGTGTCT GGGG                                          24

(2) INFORMATION FOR SEQ ID NO:39:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

CGGTTTCCTT TGCGGTC                                                  17

(2) INFORMATION FOR SEQ ID NO:40:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

GTGCTCCGGT GGCTTTTT                                                 18

(2) INFORMATION FOR SEQ ID NO:41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
         (A) NAME/KEY: misc_feature
         (B) LOCATION: 6
         (D) OTHER INFORMATION: /standard_name= "Reduced A"
```

-continued

```
    (ix) FEATURE:
         (A) NAME/KEY: misc_feature
         (B) LOCATION: 10
         (D) OTHER INFORMATION: /standard_name= "Reduced A"

(xi) SEQUENCE DESCRIPTION: SEQ ID NO:41:

GGTCCAGCCA TGGGTCTGGG                                             20

(2) INFORMATION FOR SEQ ID NO:42:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:42:

GCTGGTCCTC TGCTGTCCTT GCTG                                        24

(2) INFORMATION FOR SEQ ID NO:43:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:43:

GCCCCGTCTG CTGCTCCTCG TGCCG                                       25

(2) INFORMATION FOR SEQ ID NO:44:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_feature
         (B) LOCATION: 6
         (D) OTHER INFORMATION: /standard_name= "Reduced A"

(ix) FEATURE:
         (A) NAME/KEY: misc_feature
         (B) LOCATION: 17
         (D) OTHER INFORMATION: /standard_name= "Reduced A"

(xi) SEQUENCE DESCRIPTION: SEQ ID NO:44:

GTTTCATCTT GGCTTTATCC                                             20
```